United States Patent
Marseille et al.

(10) Patent No.: US 9,572,917 B2
(45) Date of Patent: Feb. 21, 2017

(54) DEVICES, METHODS AND SYSTEMS FOR ESTABLISHING SUPPLEMENTAL BLOOD FLOW IN THE CIRCULATORY SYSTEM

(75) Inventors: Oliver Marseille, Aachen (DE); Wolfgang Kerkhoffs, Aachen (DE)

(73) Assignee: CircuLite, Inc., Teaneck, NJ (US)

( * ) Notice: Subject to any disclaimer, the term of this patent is extended or adjusted under 35 U.S.C. 154(b) by 318 days.

(21) Appl. No.: 12/392,623

(22) Filed: Feb. 25, 2009

(65) Prior Publication Data

US 2009/0182188 A1    Jul. 16, 2009

Related U.S. Application Data

(63) Continuation of application No. PCT/US2007/076956, filed on Aug. 28, 2007.

(Continued)

(51) Int. Cl.
*A61N 1/362* (2006.01)
*A61M 1/12* (2006.01)
(Continued)

(52) U.S. Cl.
CPC ............ *A61M 1/12* (2013.01); *A61M 1/122* (2014.02); *A61M 1/3653* (2013.01);
(Continued)

(58) Field of Classification Search
CPC ............ A61B 2017/3425; A61B 2017/3488; A61M 1/12; A61M 1/122; A61M 1/3653; A61M 1/3659; A61M 25/04
USPC ........ 600/16; 607/126, 122; 604/93.01, 264; 623/1.11, 1.15, 3.1; 606/215
See application file for complete search history.

(56) References Cited

U.S. PATENT DOCUMENTS 2,935,068 A    5/1960   Donaldson
3,195,540 A    7/1965   Waller
(Continued)

FOREIGN PATENT DOCUMENTS

DE    102004019721 A1    10/2005
EP       213748 A1         3/1987
(Continued)

OTHER PUBLICATIONS

R. J. Baird, M.D. et al., Survey of Mechanical Assistance of the Circulation and the Present Status of Left-Heart Bypass, Article, pp. 340-345, 1965.

(Continued)

*Primary Examiner* — Niketa Patel
*Assistant Examiner* — Lindsey G Hankins
(74) *Attorney, Agent, or Firm* — Wood Herron & Evans LLP

(57) ABSTRACT

Devices, systems and methods for establishing a blood flow conduit between a chamber in a heart of a patient and a remote location. A blood inflow cannula having an outer surface and proximal and distal end portions. The distal end portion is configured for insertion into the chamber of the heart. First and second anchor elements have respective maximum width dimensions extending outwardly from the outer surface of the cannula. The first anchor element is positioned more distally than the second anchor element defining a tissue receiving space therebetween. The maximum width dimension of the first anchor element may be larger than the maximum width dimension of the second anchor element in use. The first anchor element is configured to be positioned inside the heart chamber and the second anchor element is configured to be positioned outside the heart chamber with heart tissue held in the tissue receiving space therebetween.

37 Claims, 14 Drawing Sheets

Related U.S. Application Data

(60) Provisional application No. 60/823,971, filed on Aug. 30, 2006.

(51) Int. Cl.

| | | |
|---|---|---|
| *A61M 1/36* | (2006.01) | |
| *A61M 25/04* | (2006.01) | |
| *A61M 25/06* | (2006.01) | |
| *A61B 17/34* | (2006.01) | |

(52) U.S. Cl.
CPC .......... *A61M 1/3659* (2014.02); *A61M 25/04* (2013.01); *A61M 25/0662* (2013.01); *A61B 2017/3425* (2013.01); *A61B 2017/3488* (2013.01)

(56) References Cited

U.S. PATENT DOCUMENTS

| | | | |
|---|---|---|---|
| 3,433,227 A | 3/1969 | Alley et al. | |
| 3,903,895 A * | 9/1975 | Alley et al. | 604/178 |
| 3,942,535 A | 3/1976 | Schulman | |
| 4,033,331 A | 7/1977 | Guss et al. | |
| 4,534,761 A | 8/1985 | Raible | |
| 4,790,825 A | 12/1988 | Bernstein | |
| 4,995,857 A | 2/1991 | Arnold | |
| 5,163,954 A | 11/1992 | Curcio et al. | |
| 5,171,218 A | 12/1992 | Fonger et al. | |
| 5,190,528 A | 3/1993 | Fonger et al. | |
| 5,256,146 A | 10/1993 | Ensminger et al. | |
| 5,287,852 A | 2/1994 | Arkinstall | |
| 5,290,227 A | 3/1994 | Pasque | |
| 5,290,251 A | 3/1994 | Griffith | |
| 5,300,107 A | 4/1994 | Stokes et al. | |
| 5,338,301 A | 8/1994 | Diaz | |
| 5,344,443 A | 9/1994 | Palma et al. | |
| 5,545,191 A | 8/1996 | Mann et al. | |
| 5,676,670 A | 10/1997 | Kim | |
| 5,695,471 A | 12/1997 | Wampler | |
| 5,697,936 A | 12/1997 | Shipko et al. | |
| 5,704,891 A | 1/1998 | Mussivand | |
| 5,711,753 A | 1/1998 | Pacella et al. | |
| 5,728,134 A * | 3/1998 | Barak | 606/214 |
| 5,738,649 A | 4/1998 | Macoviak | |
| 5,741,316 A | 4/1998 | Chen et al. | |
| 5,743,845 A | 4/1998 | Runge | |
| 5,797,960 A * | 8/1998 | Stevens et al. | 606/213 |
| 5,840,070 A | 11/1998 | Wampler | |
| 5,843,088 A | 12/1998 | Barra et al. | |
| 5,858,009 A | 1/1999 | Jonkman | |
| 5,921,971 A | 7/1999 | Agro et al. | |
| 5,924,848 A | 7/1999 | Izraelev | |
| 5,924,975 A | 7/1999 | Goldowsky | |
| 5,938,412 A | 8/1999 | Izraelev | |
| 5,941,813 A | 8/1999 | Sievers et al. | |
| 5,944,745 A | 8/1999 | Rueter | |
| 5,947,892 A | 9/1999 | Benkowski et al. | |
| 5,948,006 A | 9/1999 | Mann | |
| 5,965,089 A | 10/1999 | Jarvik et al. | |
| 6,001,056 A | 12/1999 | Jassawalla et al. | |
| 6,017,355 A | 1/2000 | Hessel et al. | |
| 6,116,862 A | 9/2000 | Rau et al. | |
| 6,176,848 B1 | 1/2001 | Rau et al. | |
| 6,186,999 B1 | 2/2001 | Chen | |
| 6,273,861 B1 | 8/2001 | Bates et al. | |
| 6,299,575 B1 | 10/2001 | Bolling | |
| 6,354,299 B1 | 3/2002 | Fischell et al. | |
| 6,358,266 B1 | 3/2002 | Bonutti | |
| 6,406,420 B1 | 6/2002 | McCarthy et al. | |
| 6,530,876 B1 | 3/2003 | Spence | |
| 6,565,536 B1 | 5/2003 | Sohn | |
| 6,605,032 B2 | 8/2003 | Benkowski et al. | |
| 6,623,475 B1 | 9/2003 | Siess | |
| 6,669,708 B1 | 12/2003 | Nissenbaum et al. | |
| 6,740,101 B2 * | 5/2004 | Houser et al. | 606/153 |
| 6,926,662 B1 | 8/2005 | Aboul-Hosn et al. | |
| 6,942,611 B2 | 9/2005 | Siess | |
| 6,955,175 B2 | 10/2005 | Stevens et al. | |
| 6,994,666 B2 | 2/2006 | Shannon et al. | |
| 7,048,681 B2 | 5/2006 | Tsubouchi et al. | |
| 7,070,555 B2 | 7/2006 | Siess | |
| 7,077,801 B2 | 7/2006 | Haverich | |
| 7,317,951 B2 | 1/2008 | Schneider et al. | |
| 7,340,288 B1 * | 3/2008 | Karicherla et al. | 600/374 |
| 7,515,971 B1 * | 4/2009 | Doan | 607/126 |
| 7,699,864 B2 | 4/2010 | Kick et al. | |
| 7,713,193 B2 | 5/2010 | Nance et al. | |
| 7,722,568 B2 | 5/2010 | Lenker et al. | |
| 7,780,692 B2 | 8/2010 | Nance et al. | |
| 2002/0010425 A1 | 1/2002 | Guo et al. | |
| 2003/0093104 A1 | 5/2003 | Bonner et al. | |
| 2004/0015150 A1 | 1/2004 | Zadno-Azizi | |
| 2004/0024285 A1 | 2/2004 | Muckter | |
| 2004/0024435 A1 | 2/2004 | Leckrone et al. | |
| 2004/0153112 A1 | 8/2004 | Nissenbaum et al. | |
| 2004/0193004 A1 | 9/2004 | Tsubouchi et al. | |
| 2004/0236170 A1 | 11/2004 | Kim | |
| 2005/0107658 A1 | 5/2005 | Brockway | |
| 2005/0124937 A1 | 6/2005 | Kick et al. | |
| 2005/0159711 A1 | 7/2005 | Kathrani et al. | |
| 2005/0288596 A1 * | 12/2005 | Eigler | A61B 5/0215 600/485 |
| 2006/0052750 A1 | 3/2006 | Lenker et al. | |
| 2006/0094983 A1 | 5/2006 | Burbank et al. | |
| 2006/0100565 A1 | 5/2006 | Aboul-Hosn | |
| 2006/0116746 A1 | 6/2006 | Chin | |
| 2006/0135946 A1 | 6/2006 | Moehle et al. | |
| 2006/0135962 A1 | 6/2006 | Kick et al. | |
| 2006/0135963 A1 | 6/2006 | Kick et al. | |
| 2006/0135981 A1 | 6/2006 | Lenker et al. | |
| 2006/0184088 A1 * | 8/2006 | Van Bibber et al. | 604/8 |
| 2006/0200189 A1 | 9/2006 | Nance et al. | |
| 2006/0235357 A1 | 10/2006 | Woodward et al. | |
| 2006/0253102 A1 | 11/2006 | Nance et al. | |
| 2008/0200943 A1 | 8/2008 | Barker et al. | |
| 2008/0215008 A1 | 9/2008 | Nance et al. | |
| 2008/0243081 A1 | 10/2008 | Nance et al. | |
| 2009/0112050 A1 | 4/2009 | Farnan et al. | |
| 2009/0254166 A1 | 10/2009 | Chou et al. | |
| 2009/0287182 A1 | 11/2009 | Bishop et al. | |
| 2009/0287183 A1 | 11/2009 | Bishop et al. | |
| 2010/0145267 A1 | 6/2010 | Bishop et al. | |
| 2010/0228077 A1 | 9/2010 | Lenker et al. | |
| 2011/0040324 A1 * | 2/2011 | McCarthy et al. | 606/215 |
| 2011/0166582 A1 * | 7/2011 | Syed et al. | 606/129 |

FOREIGN PATENT DOCUMENTS

| | | | |
|---|---|---|---|
| EP | 0 604 803 A2 | 7/1994 | |
| EP | 745409 A1 | 12/1996 | |
| EP | 1 557 130 A1 | 7/2005 | |
| JP | 6297650 U | 6/1987 | |
| JP | 62159659 A | 7/1987 | |
| JP | 10305094 A | 11/1998 | |
| JP | 2001504365 A | 4/2001 | |
| WO | 9742413 A1 | 11/1997 | |
| WO | 9819629 A2 | 5/1998 | |
| WO | 9959652 A1 | 11/1999 | |
| WO | 0180927 A2 | 11/2001 | |
| WO | 2004082742 A1 | 9/2004 | |
| WO | 2004/091716 A1 | 10/2004 | |
| WO | 2005037345 A2 | 4/2005 | |
| WO | 2008/034068 A2 | 3/2008 | |
| WO | WO2008/027869 A2 * | 3/2008 | A61M 1/10 |

OTHER PUBLICATIONS

R. J. Baird F.R.C.S.(C) et al., Le Support Mechanique Du Ventricule Gauche, Article, pp. 258-268, Dec. 1964.
World Heart Corporation, World Heart, 1998 Annual Report, 36 pgs.
U.S. Patent and Trademark Office, International Search Report and Written Opinion in PCT Application Serial No. PCT/US07/61118, Nov. 2, 2007.

(56) References Cited

OTHER PUBLICATIONS

U.S. Patent and Trademark Office, International Search Report and Written Opinion in PCT Application Serial No. PCT/US07/78507, Mar. 14, 2008.
U.S. Patent and Trademark Office, International Search Report and Written Opinion in PCT Application Serial No. PCT/US07/76956, Aug. 19, 2008.
U.S. Patent and Trademark Office, International Search Report and Written Opinion in PCT Application Serial PCT/US07/66406, Oct. 8, 2008.
U.S. Patent and Trademark Office, International Search Report and Written Opinion in PCT Application Serial No. PCT/US08/71938, Nov. 3, 2008.
U.S. Patent and Trademark Office, International Search Report and Written Opinion in PCT Application Serial No. PCT/US08/71922, Nov. 3, 2008.
O.H. Frazier, MD et al., The HeartMate® Left Ventricular Assist System, Texas Heart Institute Journal, vol. 25, No. 4, 1998, pp. 265-271.
J. Mark Burnett, RCP et al., Intracardiac Echocardiography 101: The Beginner's Guide to ICE Imaging and Cardiac Structure Recognition, http://www.eplabdigest.com/article/4148, Dec. 13, 2007.
U.S. Patent and Trademark Office, International Preliminary Examination Report in PCT Application No. PCT/ US07/76956, Feb. 4, 2009.
U.S. Patent and Trademark Office International Search Report and Written Opinion in PCT Application No. PCT/US2008/081082, Feb. 10, 2009.
U.S. Patent and Trademark Office, Written Opinion in PCT Serial No. PCT/US08/71938, Sep. 28, 2009.
U.S. Patent and Trademark Office, International Preliminary Examination Report in PCT Serial No. PCT/US08/71922, Sep. 28, 2009.
U.S. Patent and Trademark Office, International Preliminary Report on Patentability in PCT Application No. PCT/US08/71938, Apr. 1, 2010.
U.S. Patent and Trademark Office, International Preliminary Report on Patentability in PCT Serial No. PCT/US08/081082, Apr. 26, 2010.
U.S. Patent and Trademark Office, Office Action in U.S. Appl. No. 11/846,839, Apr. 29, 2010.
European Patent Office, Search Report and Examiner's Preliminary Opinion, in Serial No. EP10250524, Nov. 12, 2010.
European Patent Office, Search Report and Examiner's Preliminary Opinion, in Serial No. EP10250525, Aug. 18, 2010.
U.S. Patent and Trademark Office, Notice of Allowance in U.S. Appl. No. 11/846,839, Nov. 12, 2010.
U.S. Patent and Trademark Office, Final Office Action in U.S. Appl. No. 11/846,839, Aug. 4, 2010.
U.S. Patent and Trademark Office, International Preliminary Report on Patentability PCT Application No. PCT/US08/066406, Jan. 27, 2010.
U.S. Patent and Trademark Office, Office Action in U.S. Appl. No. 11/846,886, Apr. 12, 2011.
Japanese Patent Office, Office Action in JP Application No. 2009-526860, Aug. 7, 2012.
European Patent Office; Supplemental Search Report in European Patent Application No. 07814495.3 dated Feb. 24, 2012; 7 pages.
European Patent Office, European Search Report in Application Serial No. 13173762, Sep. 13, 2013.
Japanese Office Action, Notice of Reaspons for Rejection in JP Application No. 2013-271353, Jan. 13, 2015.
European Patent Office, European Search Report in Application Serial No. 14196639, Feb. 11, 2015.

* cited by examiner

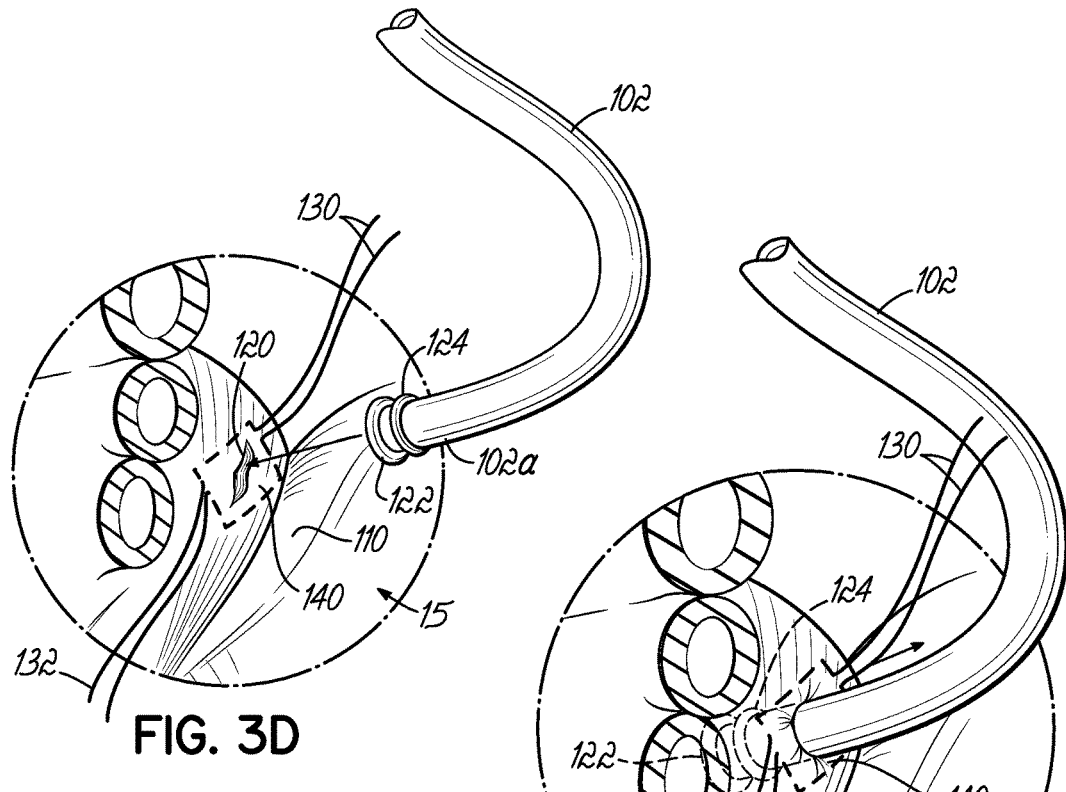
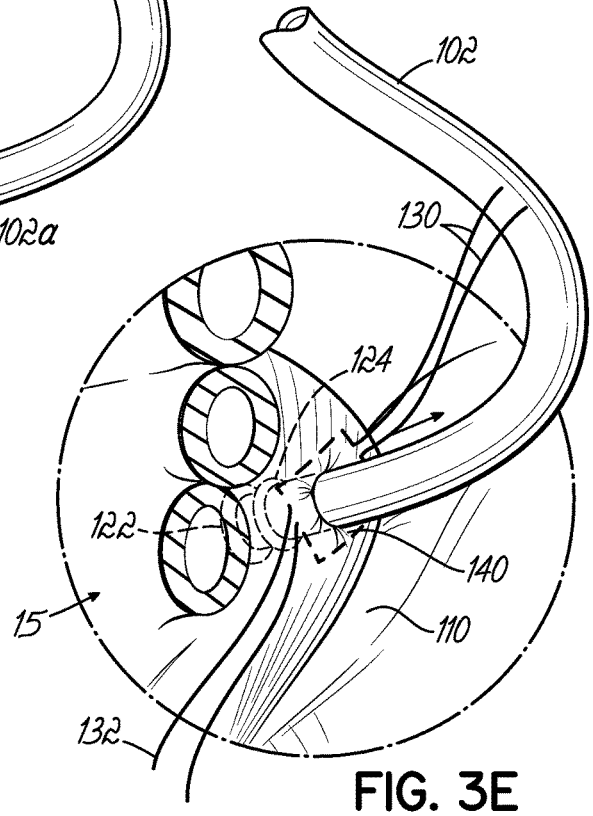
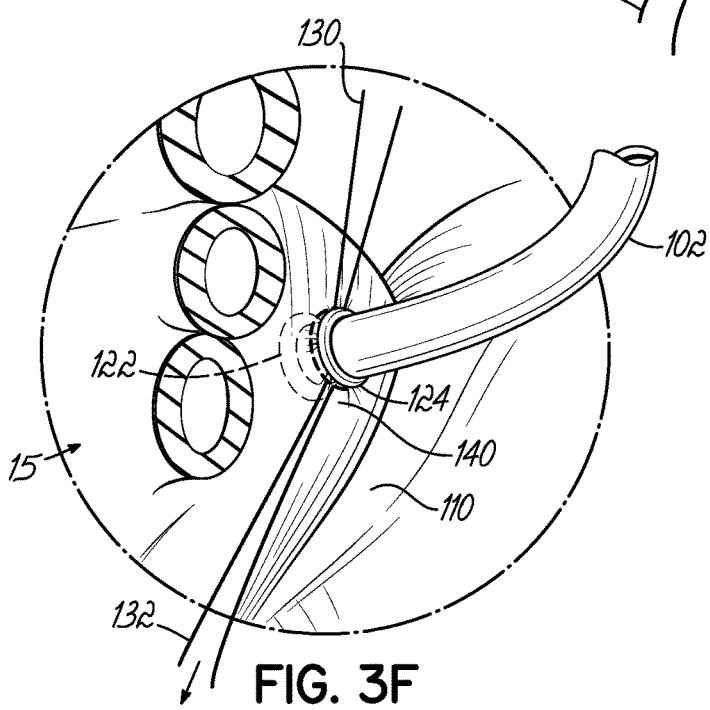
FIG. 3D
FIG. 3E
FIG. 3F

DEVICES, METHODS AND SYSTEMS FOR ESTABLISHING SUPPLEMENTAL BLOOD FLOW IN THE CIRCULATORY SYSTEM

CROSS REFERENCE

This application is a continuation of PCT Application Ser. No. PCT/US2007/076956, filed Aug. 28, 2007 (pending) which claims the priority benefit of U.S. Provisional Patent Application Ser. No. 60/823,971, filed Aug. 30, 2006 (expired), the disclosures of which are incorporated by reference herein in their entirety.

TECHNICAL FIELD

This invention generally relates to medical devices and methods and, more particularly, to methods and devices for fluid coupling to the heart of a patient in systems for assisting blood circulation in a patient.

BACKGROUND

Various devices and methods have been utilized to conduct blood from the heart to assist with blood circulation in a patient. This is often desirable or necessary in cases where a patient is experiencing congestive heart failure and a transplant organ has either not been located, or the patient is not a suitable candidate for a transplant. The blood pumps are typically attached directly to the left ventricle of the heart, however, at least one blood pump system locates the pump remotely, such as subcutaneously in the manner of a pacemaker. In this regard, see U.S. Pat. No. 6,530,876, the disclosure of which is hereby fully incorporated by reference herein. In this situation or similar situations, a cannula may be used to create an inflow conduit from the heart (an intra-thoracic location) to a pump located in a superficial (non-thoracic cavity) location, which may be the so-called "pacemaker pocket." Of course, other remote locations are possible as alternatives. The pacemaker pocket is a location usually accessed by a surgical incision generally parallel to and below the collarbone extending down toward the breast, and over the pectoral muscle. Sometimes the pacemaker pocket is made below the muscle. The pump, to which the cannula is connected, is intended to sit in the pectoral pocket, and is preferably but not limited to the right side of the chest.

One area in need of improvement is the anchoring mechanism used to fluidly connect the inflow conduit or cannula to the heart. The cannula can be connected and anchored to any chamber of the heart from which it is desired to conduct or conduit blood. One anchor point is the left side of the heart, such as the left atrium. This is shown in U.S. Pat. No. 6,530,876. It would be desirable to ensure that this connection is as secure and leakage free as possible. In addition, the procedure for making the connection should be as simple as possible under the circumstances.

General cannula implantation methods known and usable in connection with the present invention may involve many different approaches and several of the representative approaches are described further below. For example, the cannula may be implanted by directly invading the thoracic cavity. Other surgical methods include so-called open heart surgery in which a median sternotomy is made to fully expose the heart within the thoracic cavity. Still other surgical methods include less invasive surgical methods such as a thoracotomy, mini-thoracotomy, thoracoscopic, or any other less invasive approaches. Any of these surgical methods can be used to implant the cannula in fluid communication with any desired location of the heart as described herein.

Alternatively, a transluminal method of implanting the cannula may be used in which the thoracic cavity is not invaded directly, but rather the heart is accessed utilizing blood vessels naturally connecting into the heart. Transluminal methods include so-called transvenous delivery of the cannula to the left side of the heart via the right side of the heart to which the major veins and the more distal peripheral veins provide natural conduits through which the cannula can be delivered. In this approach, the cannula may more precisely be referred to as a catheter. Transluminal methods generally utilize indirect visualization, such as by means of contrast-dye enhanced fluoroscopy and/or ultrasonic imaging to navigate devices through the vessels of the body.

SUMMARY

Generally, and in one of many alternative aspects, the present invention provides a device for establishing a blood flow conduit between a chamber in a heart of a patient and a remote location, such as a location at which a blood pump resides away from the heart. In this regard, the term "remote," as used herein means away from the heart but is not limited to any particular distance from the heart. The device comprises an inflow cannula having an outer surface and proximal and distal end portions (relative to a surgeon implanting the cannula). The distal end portion is configured for insertion into the chamber of the heart. First and second anchor elements having respective maximum width dimensions extend outwardly from the outer surface of the inflow cannula at its distal end portion. The first anchor element is positioned more distally than the second anchor element and a tissue receiving space is defined between the first and second anchor elements. The maximum width dimension of the first anchor element is larger than the maximum width dimension of the second anchor element in this aspect of the invention. The first anchor element is configured to be positioned inside the heart chamber and the second anchor element is configured to be positioned outside the heart chamber with heart tissue held in the tissue receiving space therebetween. As with the other devices/systems of this invention, this device may be installed in a patient through any suitable type of surgical procedure.

In another aspect of the invention, the device as generally described immediately above is implemented in a catheter based system. In this aspect, the inflow cannula is more specifically a blood inflow catheter and the inflow catheter is configured to be directed into the venous system of the patient. The inflow catheter may be received by the delivery catheter for purposes of establishing the blood inflow conduit in a minimally invasive manner.

In another aspect of the invention, the devices and systems of the present invention may further include a blood pump having an inlet and an outlet. The outlet is adapted for connection to a remote location in the circulatory system of the patient via an outflow cannula or catheter and the inlet is adapted for connection to the inflow cannula.

In another aspect, the invention provides a method of establishing blood flow from a chamber in a heart of a patient to a remote location for providing supplemental blood flow from the heart. The method may comprise inserting at least a portion of a distal end portion of an inflow cannula into the chamber of the heart. The distal end portion includes first and second anchor elements each having a maximum width dimension in a direction perpendicular to a lengthwise axis of the inflow cannula, and the first anchor element has a larger maximum width dimension than the second anchor element. The method further comprises placing the first anchor element inside the chamber and against an inside surface of tissue defining the chamber, and placing the second anchor element outside the chamber and against an outside surface of the tissue defining the chamber.

In another method performed in accordance with the inventive aspects, a distal end portion of an inflow cannula is inserted into a chamber of the heart and includes first and second anchor elements with the first anchor element being located more distally than the second anchor element, and with a tissue receiving space located between the first and second anchor elements. This method further comprises pulling the more proximally located second anchor element out of the chamber. The more proximally located second anchor element is engaged against an outside surface of tissue defining the chamber, while the first anchor element is left inside the chamber to engage an inside surface of the chamber such that the tissue is retained in the tissue receiving space and the cannula is in fluid communication with the chamber. If needed, various manners of further securing the tissue between the anchor elements may be used. One manner may be the use of one or more purse string type suture connections.

Various additional features and aspects of the embodiments and scope of the invention will be more readily appreciated upon review of the following detailed description of the illustrative embodiments taken in conjunction with the accompanying drawings.

BRIEF DESCRIPTION OF THE DRAWINGS

FIG. 1A-1 is similar to FIG. 1A, but illustrates another representative and illustrative cannula or catheter pathway.

FIG. 3D is an enlarged view of the access location or area of the heart illustrating two purse string sutures applied around a small incision for receiving the distal end or tip portion of the inflow cannula.

FIG. 3E is an enlarged view similar to FIG. 3D, but illustrating the distal end portion of the inflow cannula completely inserted into the left atrium of the heart through the incision.

FIG. 3F is a view similar to FIG. 3E, but illustrating the distal end portion of the inflow cannula partially pulled back and the purse string sutures tightened.

DETAILED DESCRIPTION OF THE ILLUSTRATIVE EMBODIMENTS

Figure 1A:
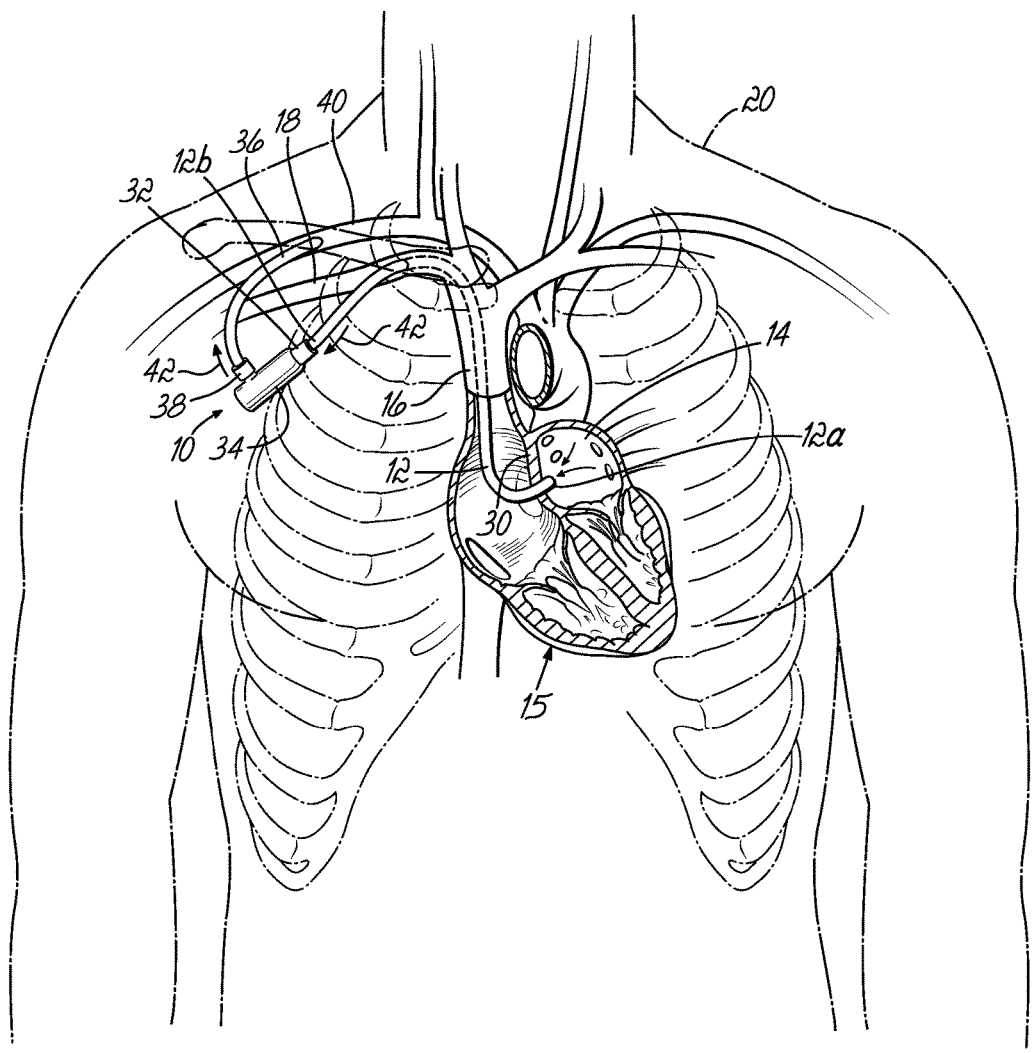
FIG. 1A is a schematic representation of chest anatomy, and illustrates one example of a pathway in the venous system used to access a patient's heart.

FIG. 1A illustrates one of many possible general configurations of a blood circulation assist system 10 implanted in accordance with the inventive aspects. Devices and systems configured in accordance with the teachings herein may be implanted in any suitable surgical manner, including but not limited to those discussed generally herein. FIG. 1A shows the system 10 implanted in a transvenous endoluminal manner and, in particular, illustrates an inflow cannula 12 passing through the venous system into the left atrium 14 of the heart 15 via the superior vena cava 16 and subclavian vein 18. Because cannula 12 passes through the venous system, it is more particularly referred to herein as a catheter 12. The inflow catheter 12 exits at a site near the clavical of the patient 20. The distal end 12a of the catheter 12 is positioned across the interatrial septum 30 generally at the location of the fossa ovalis such that the distal tip 12a of the catheter 12 is within the left atrium 14. Access may be made, for example, into any portion within the left side of the heart (e.g., the left atrium and/or left ventricle) to access oxygenated blood. The proximal end 12b of the catheter 12 is coupled to the inlet 32 of a blood pump 34. As further shown, any suitable blood pump 34 may be used, including those described in U.S. Pat. Nos. 6,176,848; 6,116,862; 6,942,611; and 6,623,475 or DE 10 2004 019 721.0. An outflow catheter 36 is connected between the outlet 38 of the pump 34 and an artery, such as the superficial axillary artery 40. Blood flow therefore travels in the direction of the arrows 42 from the left atrium 14, through the pump 34, and into the patient's arterial system through the outflow catheter 36.

Figures 1, 1A:
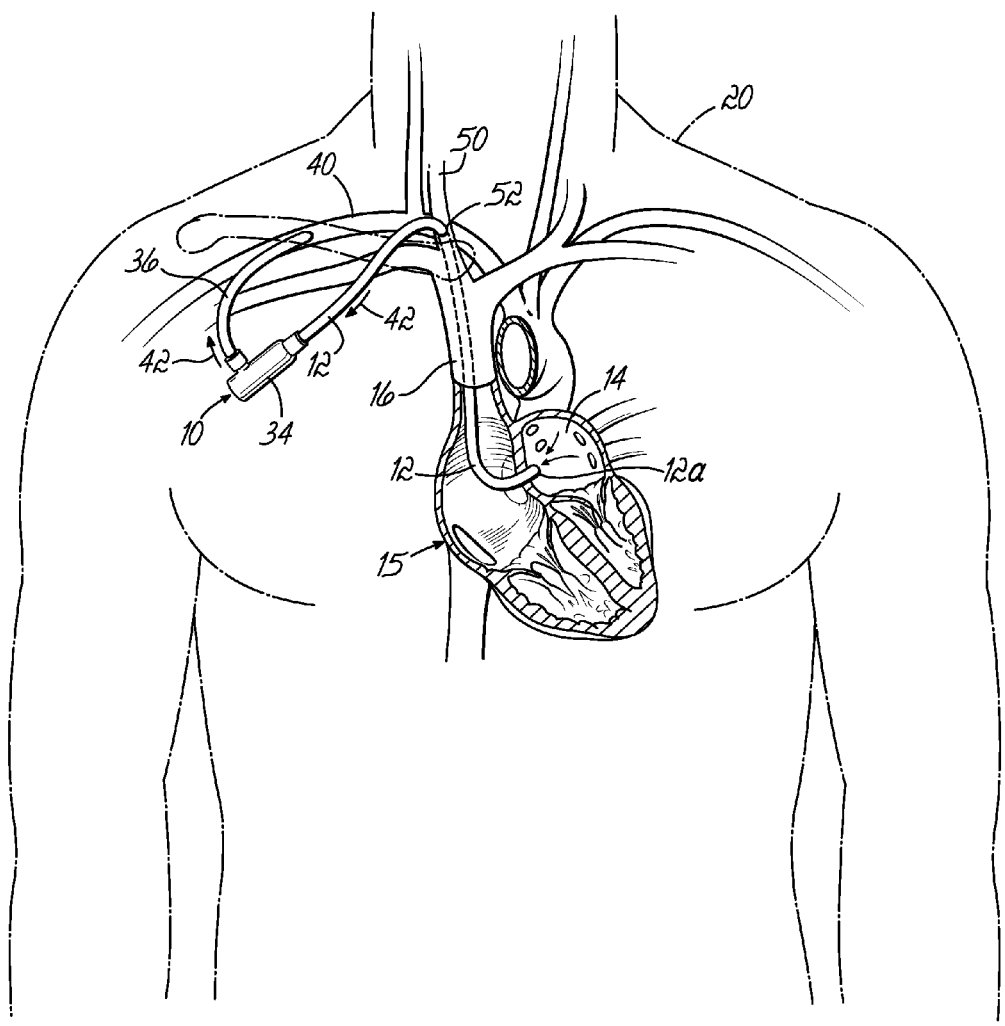

FIG. 1A-1 illustrates an alternative system configuration in which the transvenous endoluminal implantation is performed via the jugular vein 50. The inflow catheter 12 is brought from the jugular venous exit site 52 along a subcutaneous tunnel formed from the pectoral pocket where the pump 34 is situated. While the system implantation configurations shown in FIGS. 1A and 1A-1 are representative and desirable, it will be appreciated that many other implantation configurations and schemes may be implemented depending on, for example, the needs of any particular patient or desires of the surgeon.

Figure 1B:
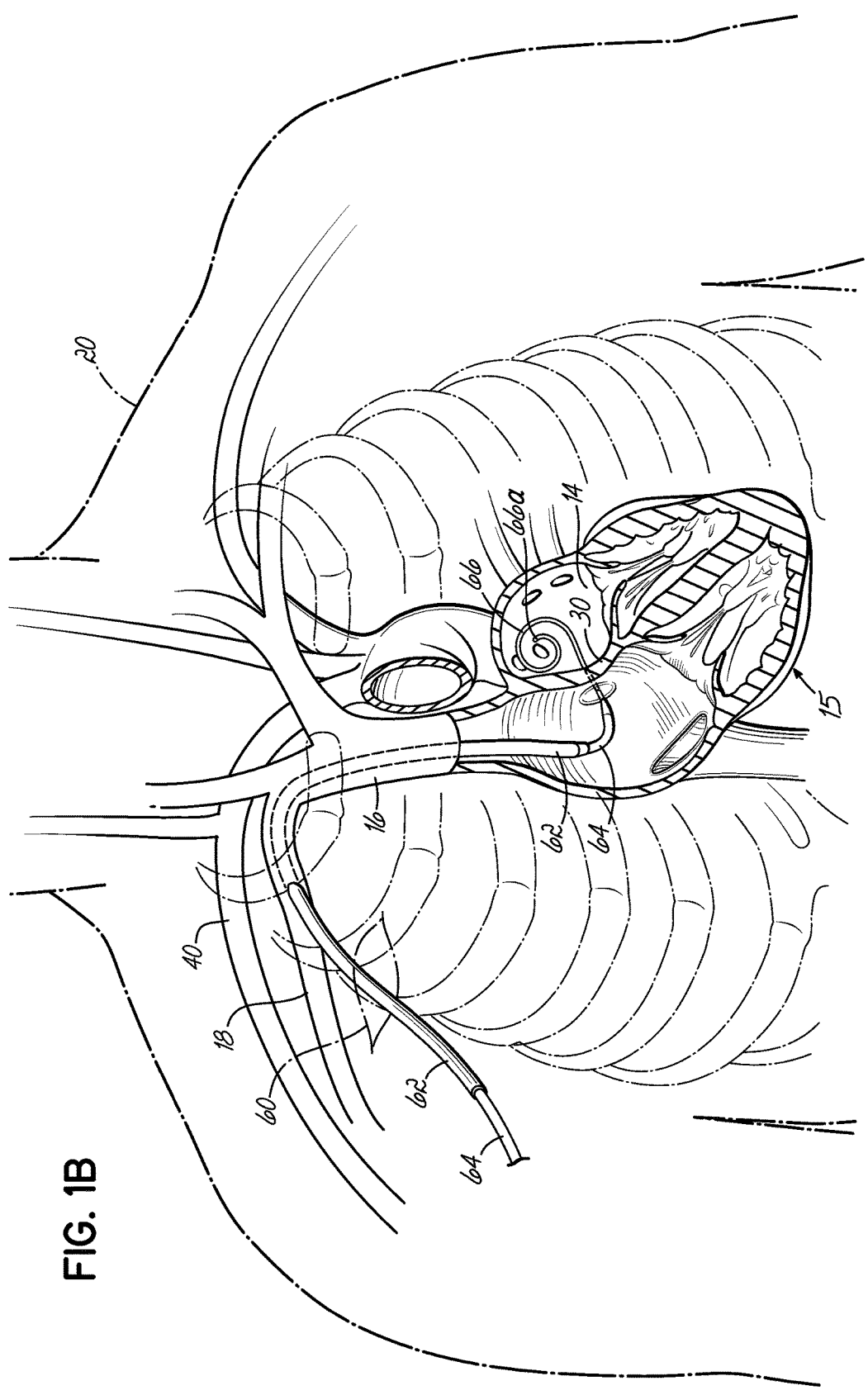
FIG. 1B is an enlarged view of the chest anatomy, including the heart, and illustrates an initial step in establishing a pathway to the left atrial chamber or left atrium of the heart.
Figure 1C:
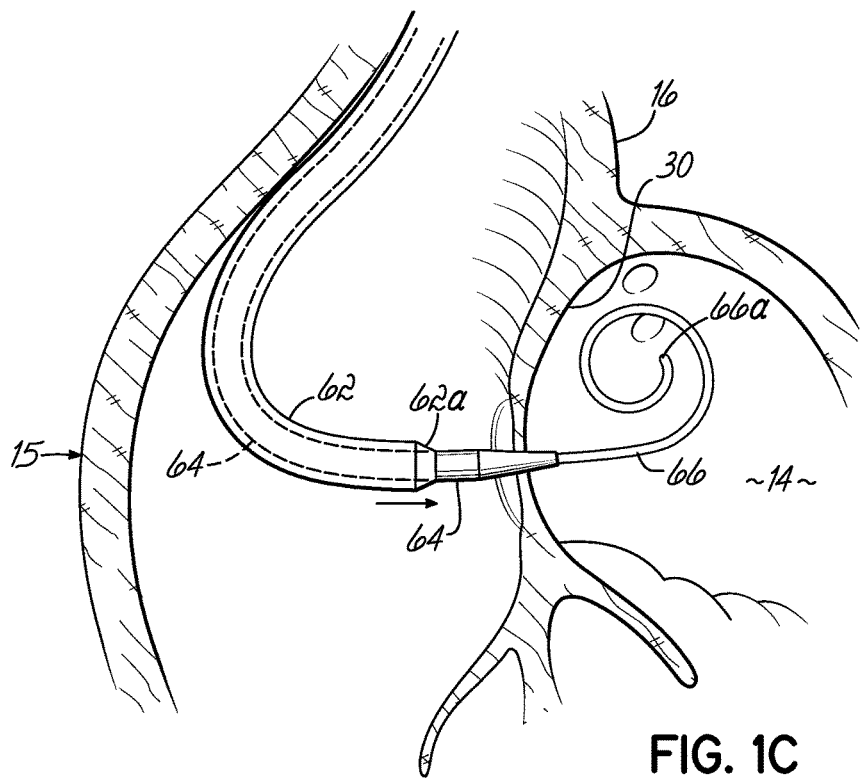
FIG. 1C illustrates an enlarged view of the heart and the catheter devices used during the initial portions of the procedure.
Figure 1D:
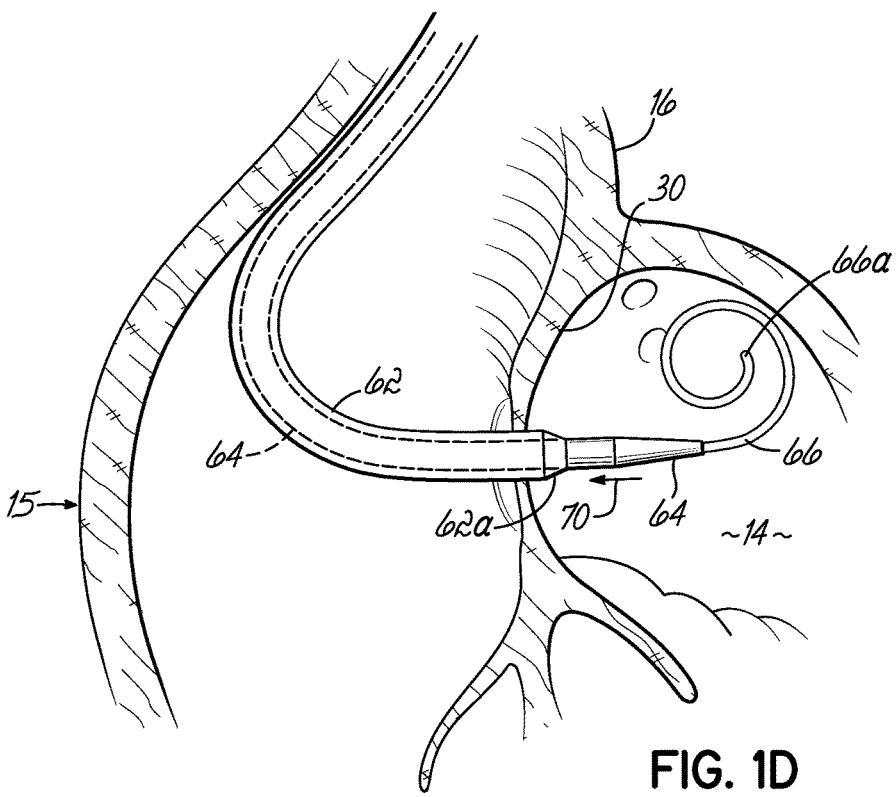
FIG. 1D is a view similar to FIG. 1C, but illustrating a subsequent portion of the procedure.

FIGS. 1B-1D illustrate in a sequential fashion the technique and components used to perform a transeptal puncture into the left atrium 14. For this application, the procedure may start from a subclavicular pectoral cut down 60 similar to that used for implantation of a pacemaker. More specifically, FIG. 1B illustrates a transceptal system including a sheath or delivery catheter 62 and a dilator device 64 received in the delivery catheter 62. In this method, a needle (not shown) may be initially used to puncture the interatrial septum 30 generally at the location of the fossa ovalis. This needle may then be exchanged for a guidewire 66 that is directed into the left atrium 14 through the dilator device 64. FIG. 1C illustrates the step of advancing the dilator 64 across the interatrial septum 30 over the guidewire 66. The guidewire 66 is typically looped within the left atrium 14 to help avoid any trauma to the heart tissue by the distal tip 66a of the guidewire 66. FIG. 1D illustrates the subsequent steps of advancing the transceptal sheath or delivery catheter 62 across the septum 30 (i.e., the tissue structure between the atrial chambers) and then retraction of the dilator 64 as illustrated by the arrow 70. The dilator 64 is completely removed leaving behind the sheath or delivery catheter 62 with the distal tip 62a located in the left atrium 14 and the guidewire 66 for use during the next step of the procedure to deliver the inflow catheter 12.

Figure 1E:
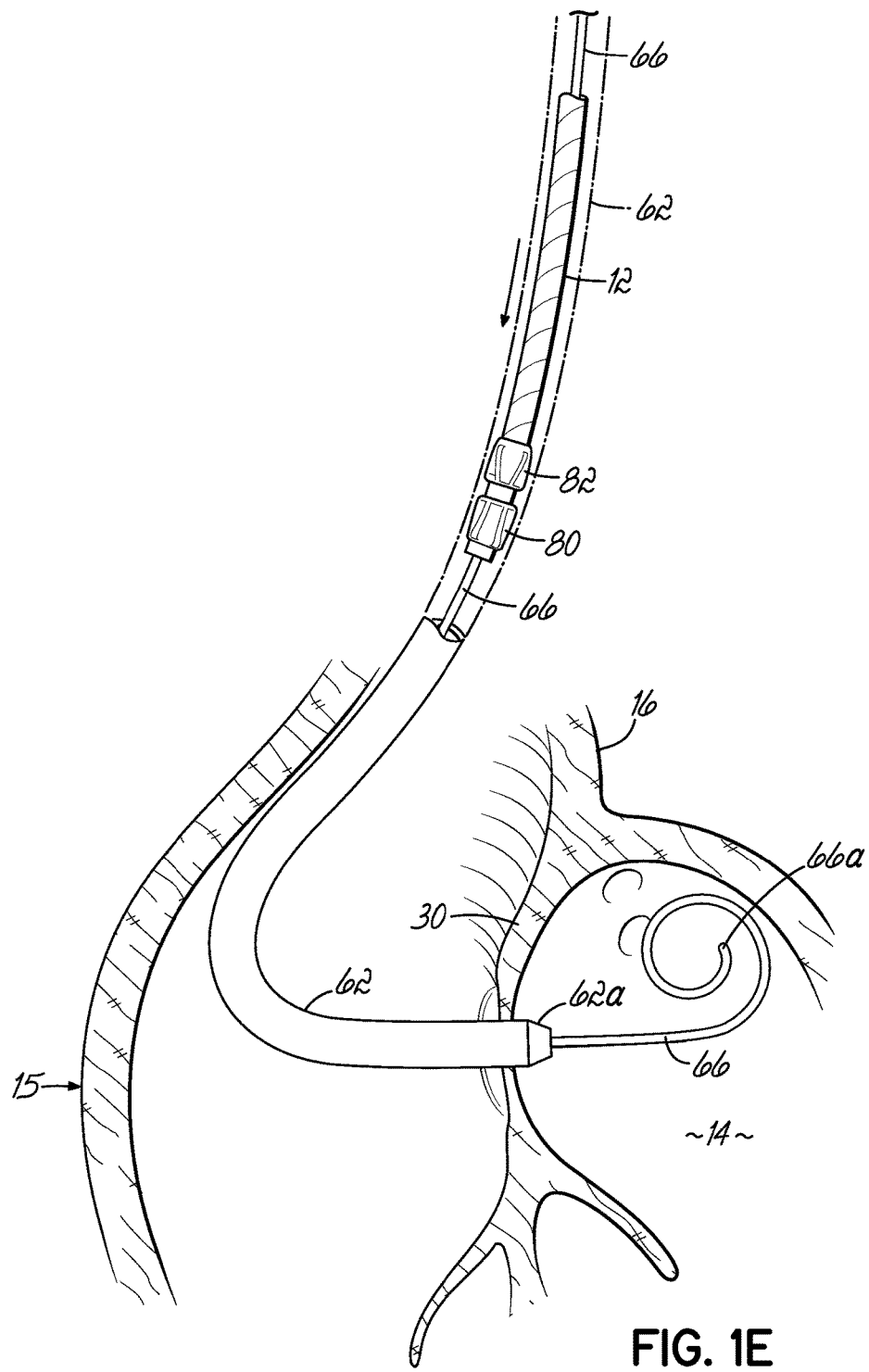
FIG. 1E is a view similar to FIG. 1D, but illustrating a subsequent portion of the procedure.

As shown in FIG. 1E, the inflow catheter 12, which is the pump inflow catheter of the system, may be introduced over the guidewire 66 and through the transceptal delivery catheter or sheath 62. The inflow catheter 12 includes first and second anchor elements 80, 82 fixed thereto with the first anchor element 80 being located more distally on the inflow catheter 12 than the second anchor element 82. In this configuration, the anchor elements 80, 82 may be retained in a compact state during delivery through the delivery catheter or sheath 62 and may be expanded either selectively or automatically as they emerge from the delivery catheter 62 during a subsequent step or steps.

Figure 1F:
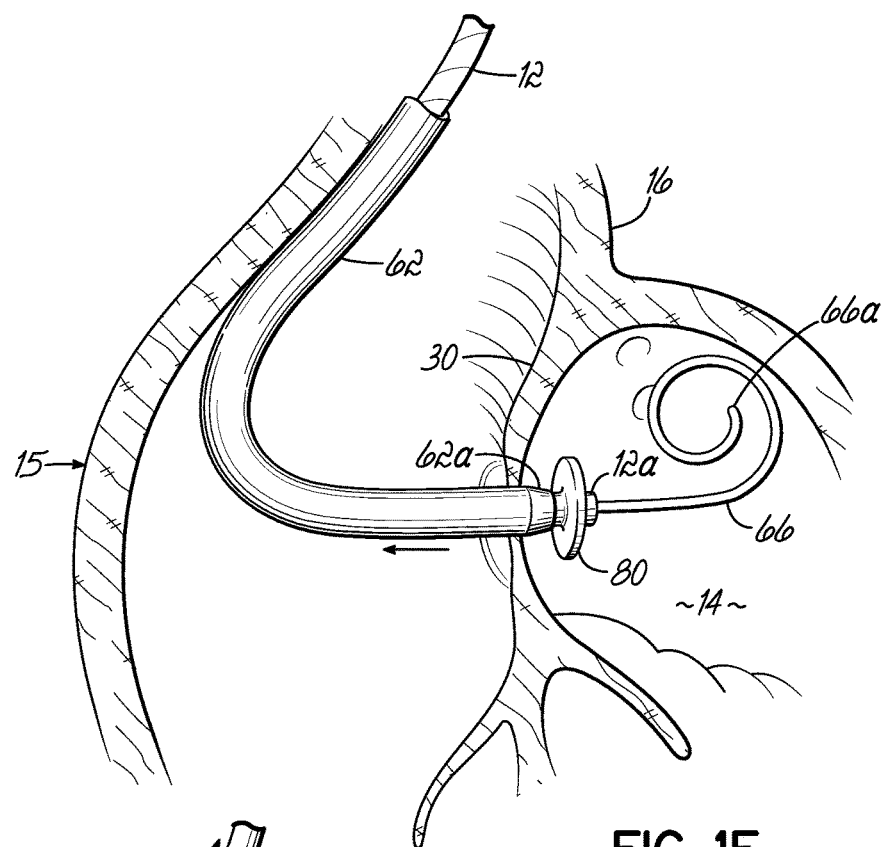
FIGS. 1F-1H are views similar to FIGS. 1C-1E, but illustrate subsequent procedural steps involved with anchoring a blood inflow catheter to a wall of the left atrium.
Figure 1G:
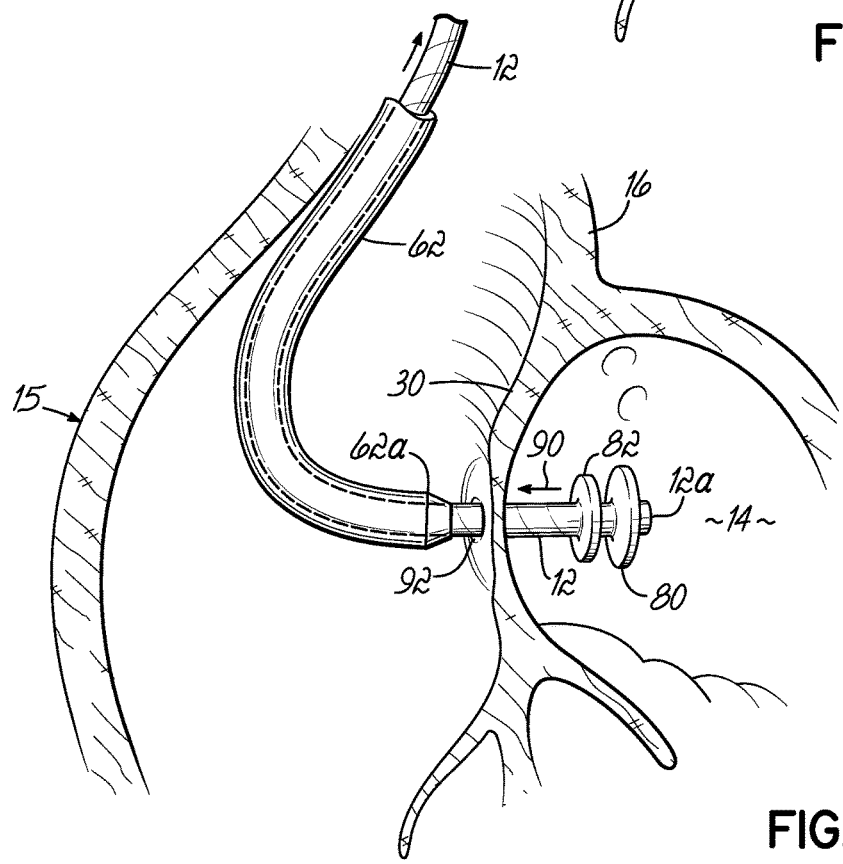
Figure 1H:
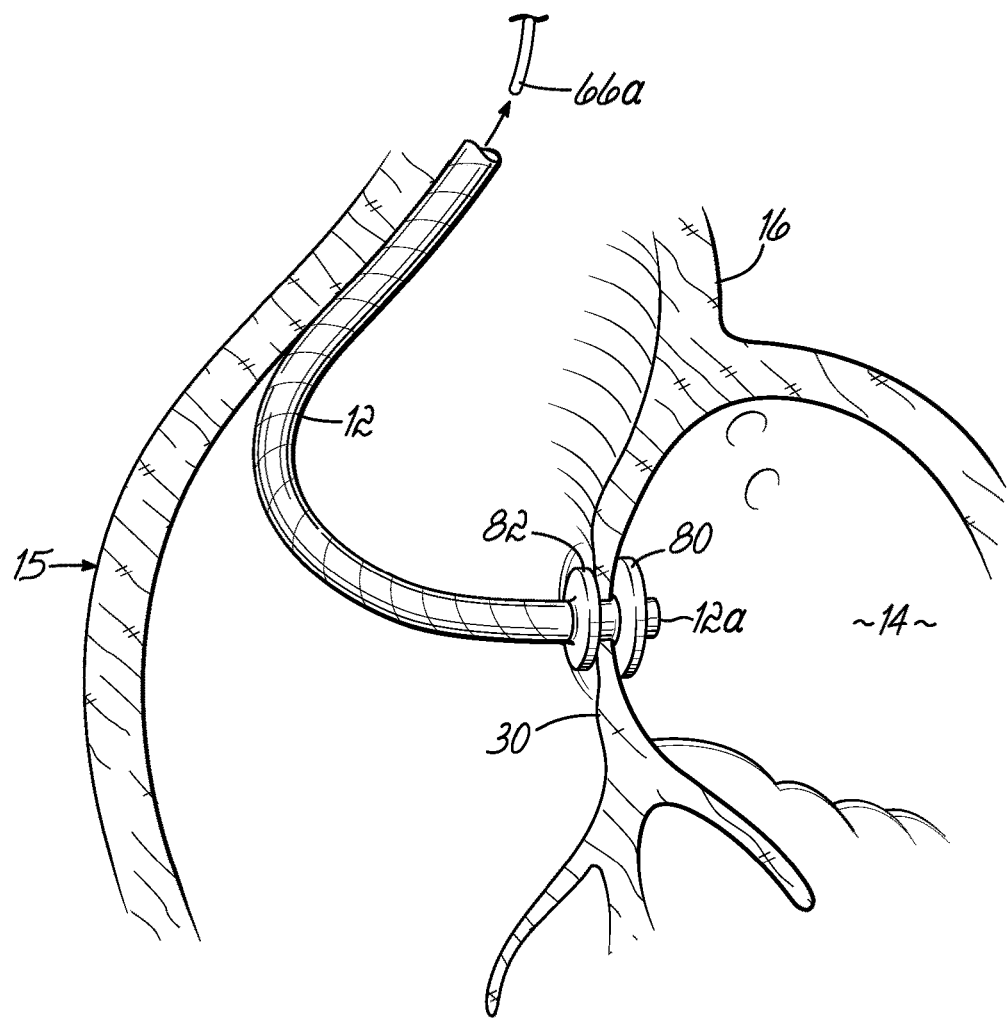
Figure 1I:
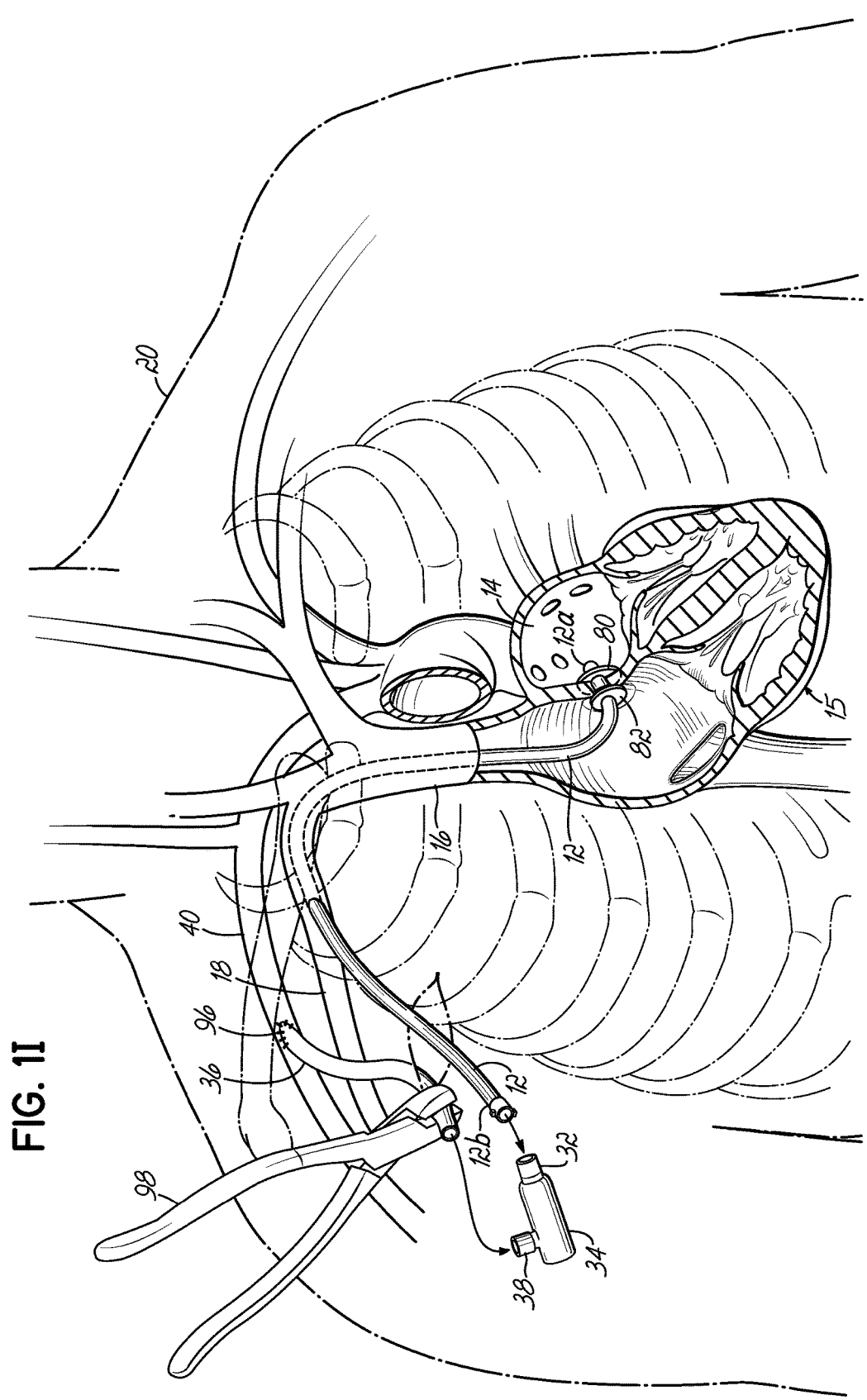
FIG. 1I is a view similar to FIG. 1B, but illustrates a step of attaching a supplemental blood flow pump to proximal ends of the inflow and outflow catheters.

FIG. 1F illustrates the inflow catheter 12 is advanced until the most distal anchor element 80, that is, the first anchor element, is deployed within the left atrium 14 from the distal tip 62a of the delivery catheter 62. In this aspect, the first or distal anchor element 80 may automatically expand due to an expanding mechanism associated therewith or due to the characteristics of the material forming the anchor element 80 itself as the anchor element 80 emerges from the delivery catheter 62. Alternatively, a mechanism may be implemented for operation by the surgeon to selectively expand one or both anchor elements 80, 82 as desired during the procedure. As shown in FIG. 1G, both anchor elements 80, 82 may be deployed within the left atrium 14 as the inflow catheter 12 is pushed out from the distal tip 62a of the delivery catheter or sheath 62. Then, as indicated by the arrow 90 in FIG. 1G, the inflow catheter 12 is pulled proximally until the second anchor element 82 is pulled through the aperture 92 created in the interatrial septum 30 and resides against the outside surface (relative to the left atrial chamber) of the interatrial septum 30 as shown in FIG. 1H. For purposes of assisting transfer of the second or proximal anchor element 82 across the interatrial wall or septum 30 and providing perceptible feedback to the surgeon, the second anchor element 82 may be formed with a smaller maximum width dimension than the first anchor element 80. For example, anchor element 80 may have an expanded diameter of 14 mm while element 82 has an expanded diameter of 12 mm, in the case in which elements 80, 82 are substantially circular discs. This ensures that the smaller anchor element 82 may noticeably pop through the aperture 92 in the interatrial septum 30 leaving the larger anchor element 80 as a firm stop against the opposite side of the septum 30 within the left atrium 14. The resulting connection will generally appear as shown in FIG. 1H, although it will be appreciated that the anchor elements 80, 82 themselves may be of various shapes, designs and configurations, and the distal end 12a of the inflow catheter 12 may or may not extend from the first anchor element 80 into the left atrium 14, as shown, but may instead be flush with the atrial side of the anchor element 80, or otherwise configured and shaped in any suitable manner.

Figure 1J:
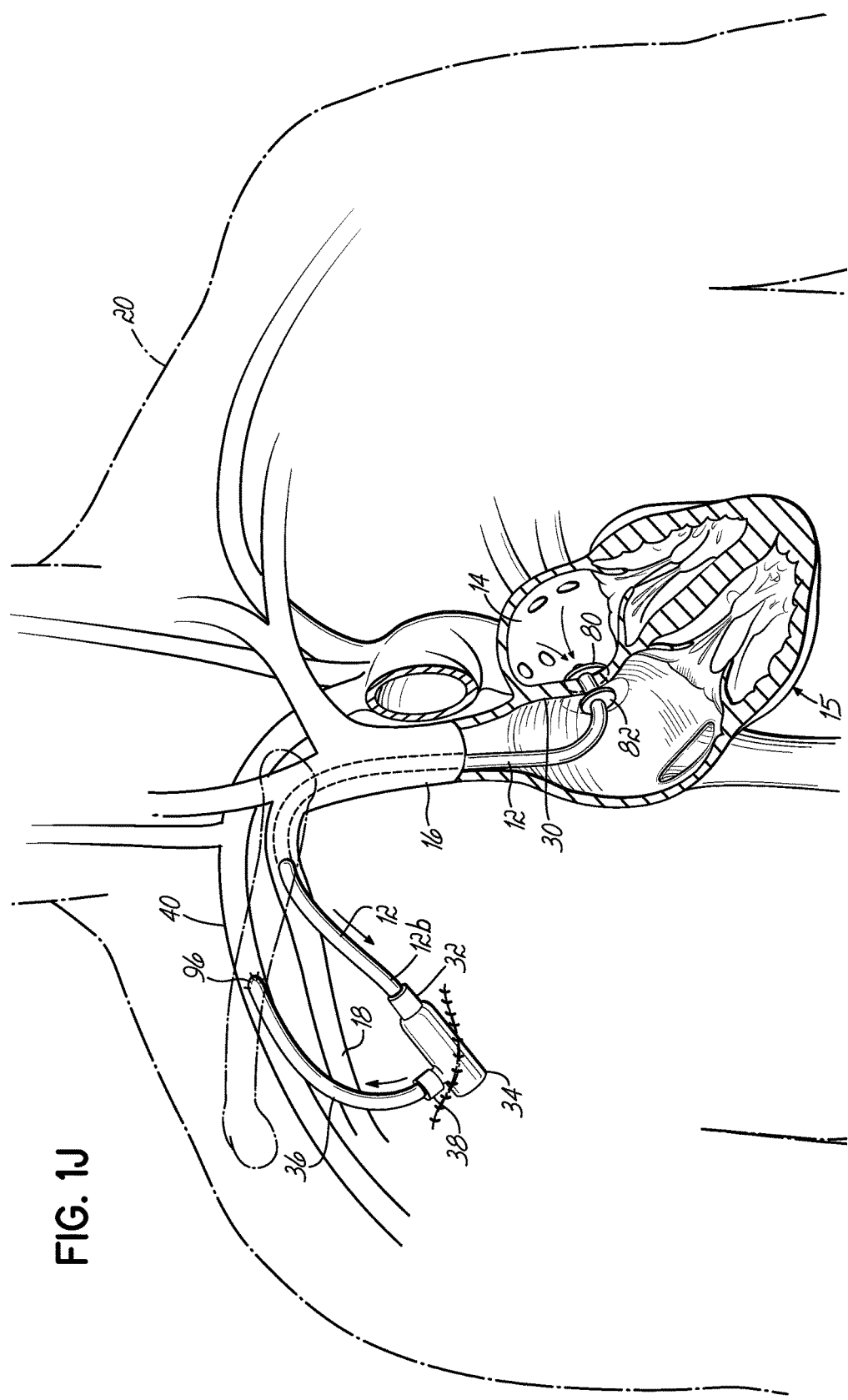
FIG. 1J is a view similar to FIG. 1I, but illustrates the fully implanted system with the supplemental blood flow pump implanted superficially in a pacemaker pocket location.

To complete the system, an outflow catheter 36 is connected to the arterial system of the patient 20, such as illustrated. For example, the outflow catheter 36 may be connected to the axillary artery 40 through a suitable surgical incision and attachment procedure which may involve the use of suitable grafts and suturing 96. A supplemental blood flow pump 34, having an inlet 32 and an outlet 38 is coupled to the inflow and outflow catheters 12, 36. The inflow and/or outflow catheters 12, 36 may first be cut to a suitable length by an appropriate sterilized cutting tool 98 such that the system may be more easily implanted into, for example, a pectoral pacemaker pocket without kinking of catheters 12, 36 as illustrated in FIG. 1J.

Figure 2:
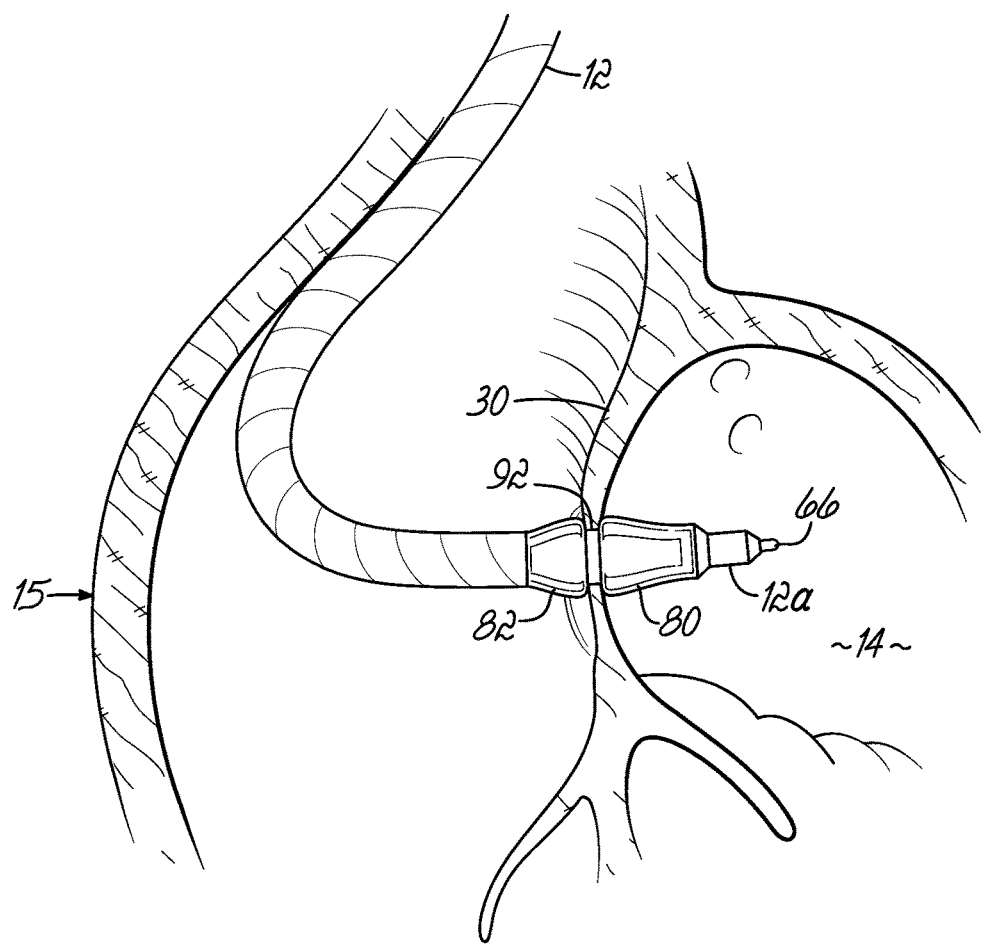
FIG. 2 is a view similar to FIG. 1H, but illustrating another alternative embodiment of the anchoring system and method of anchoring the inflow catheter to the heart tissue.

With reference to FIG. 2, like reference numerals indicate like elements as described above. FIG. 2 illustrates an alternative anchoring method in which the first and second anchor elements 80, 82 may reside on opposite sides of the tissue in a compact state, as shown, and then be selectively enlarged to anchor against and seal against the tissue which, in this example, is again the interatrial septum 30. As another alternative, the first anchor element 80 which resides in the left atrium 14 (or other location in the left side of the heart) may be expanded and seated against the inside surface of the atrium 14 as the second anchor element 82 is pulled back through the aperture 92 in its compact state. The second anchor element 82 may then be expanded against the outside surface of the septum 30 (relative to the left atrial chamber 14). In this embodiment, as with the previous embodiment, the anchor elements 80, 82 may or may not be differently sized.

As mentioned above, the anchor elements 80, 82 may comprise any suitable configuration and may involve any suitable deployment method. One desirable shape is a disc-shaped element that acts as a flange extending around the outside of the blood inflow cannula 12 and capable of forming a fluid tight seal against the heart tissue. The material of the anchor elements 80, 82 may be, for example, a pliable and/or resilient material such as surgical grade silicone. Alternatively, any other material(s) may be used. For example, materials may be used that promote ingrowth of tissue or that are covered by a material that promotes ingrowth of tissue. The anchor elements may be self-expandable when removed from the delivery catheter 62 or may be expanded by any suitable mechanism operated by the surgeon. Other restraining members aside from the delivery catheter 62 may be used as well to initially restrain the anchor elements 80, 82 in compact states during delivery to the attachment or anchoring site and optionally during initial portions of the anchoring procedure.

Figure 3A:
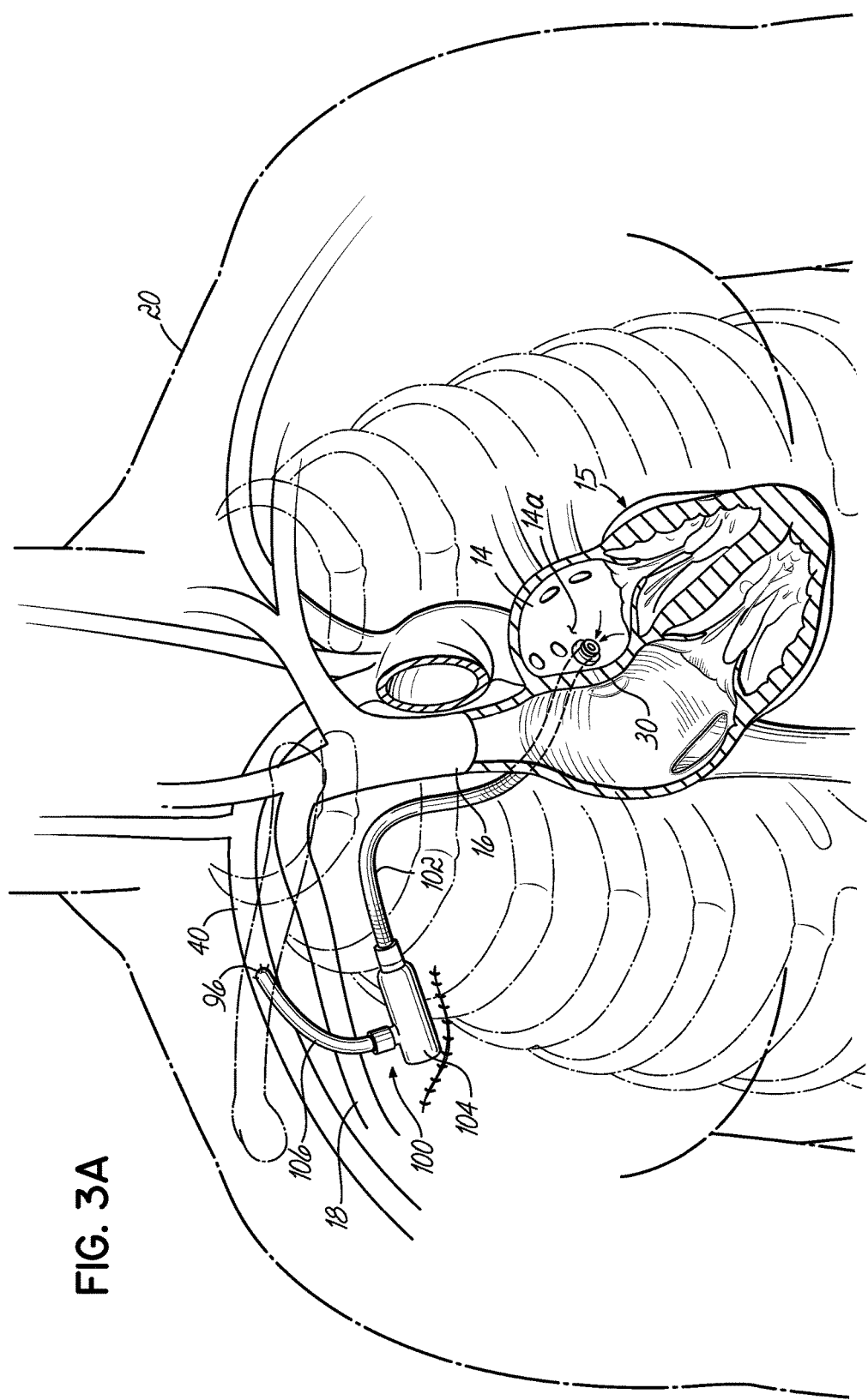
FIG. 3A is a schematic representation of chest anatomy, and illustrates an example of another pathway, exterior to the venous system, used to access a patient's heart and implant a circulatory assist system in accordance with another embodiment of the invention.
Figure 3B:
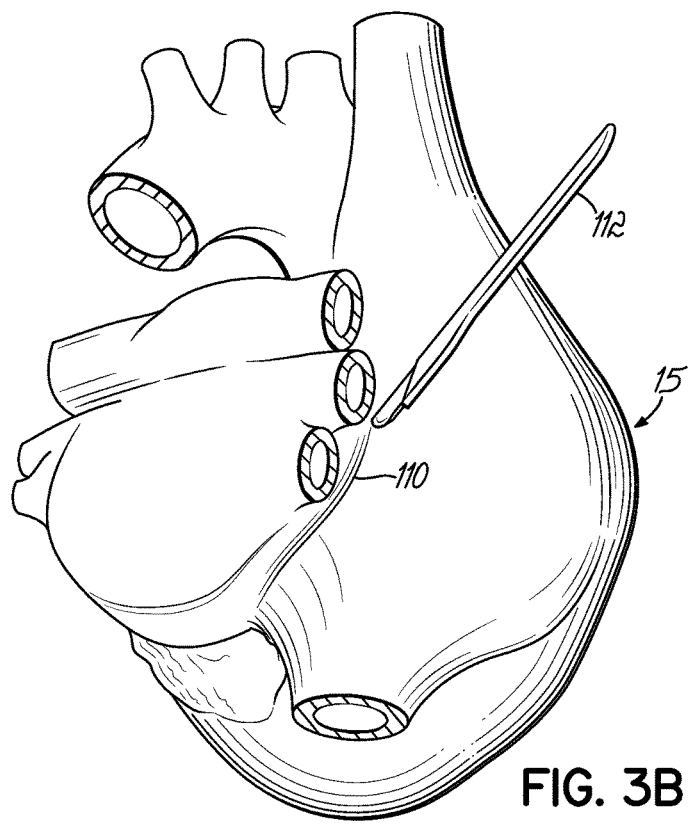
FIG. 3B is an enlarged view of the heart illustrating a location at which an incision may be made to expose an access location to the interior of the heart.

FIG. 3A illustrating a fully implanted circulatory assist system 100 in accordance with another embodiment. Again, like numerals in the drawings described below represent like elements as previously described. Specifically, this system 100 comprises an inflow cannula 102, a blood pump 104, and an outflow cannula 106. The outflow cannula 106 may be connected to a superficial artery, such as the axillary artery 40 as previously described through the use of grafts (not shown) or in other suitable manners. The inflow cannula 102 is attached directly to an exterior wall of the heart 15 on the left side, such as to the left atrial wall 14a, as shown. The inflow cannula 102, instead of being directed through the patient's venous system, is instead directed to this exterior area of the heart 15 through any desired surgical approach, such as one of the approaches generally discussed below. Once implanted, the operation of the system 100 is similar to that described above in terms of drawing oxygenated blood from the left side of the heart 15 into the inflow cannula 102, through the pump 104, and out to the arterial system via the outflow cannula 106.

Figure 3C:
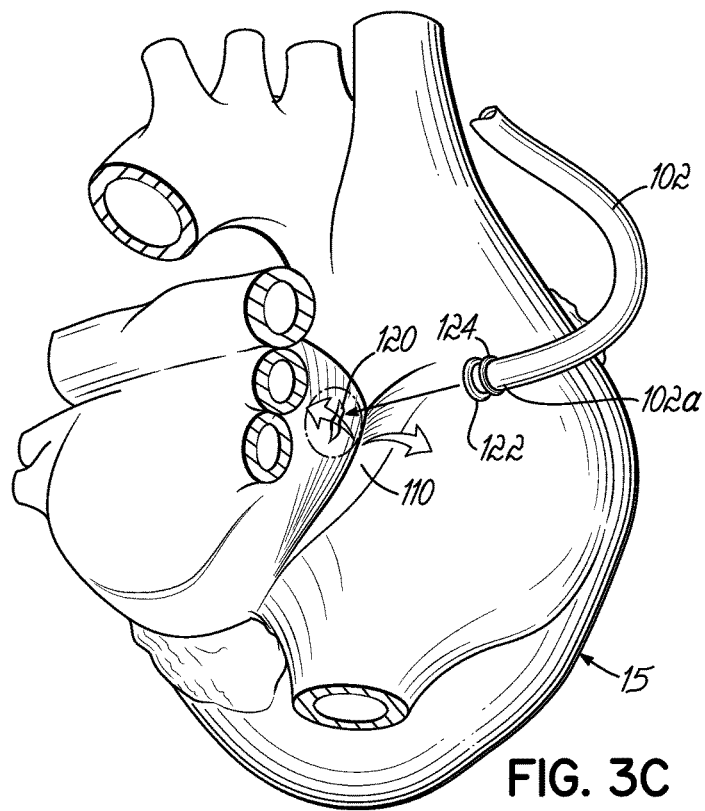
FIG. 3C is a view similar to FIG. 3B, but illustrating the access location exposed and generally showing an inflow cannula being directed toward the access location.

More specifically referring to FIGS. 3B-3F, one illustrative procedure for connecting the inflow cannula 102 is shown. In this regard, an access location 110 such as the so-called Waterson's groove is exposed or otherwise accessed during a surgical procedure. An incision may be made with a scalpel 112 to expose the access location further. As shown in FIG. 3C, a small incision 120 is made to access the interior of the left atrium 14 so as to allow for the insertion of the distal end portion 102a of the inflow cannula 102. The distal end portion 102a of the inflow cannula 102 includes distal and proximal anchor elements 122, 124 similar to those previously described, however, other designs and configurations may be used instead. As shown in FIG. 3D, one or more purse string sutures 130, 132 may be secured around the incision 120 in preparation for the insertion of the cannula 102, or after the insertion of the cannula 102. The inflow cannula 102 may be inserted through the incision 120 such that both the distal and proximal anchor elements 122, 124 are within the left atrium 14 as shown in FIG. 3E. Then, as shown in FIG. 3F, the inflow cannula 102 is withdrawn slightly proximally (toward the surgeon) to position the proximal anchor element 124 outside the left atrium 14 but leaving the distal anchor element 122 within the left atrium 14. At this time, the purse string suture or sutures 130, 132 may be tightened and tied off to fully secure the tissue 140 between the distal and proximal anchor elements 122, 124 to provide a fluid tight or at least substantially fluid tight seal. It will be appreciated that any other aspects of the previously described embodiment may be used in this embodiment as well, such as the use of various materials including surgical grade silicone for the inflow cannula 102 and anchor elements 122, 124, with or without tissue ingrowth material to further aide in providing a leak tight connection to the left atrial chamber.

Figure 4A:
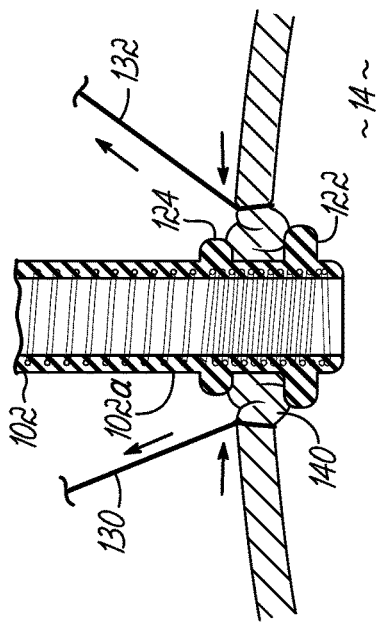
FIGS. 4A and 4B are respective cross sectional views of the access location with the inflow cannula distal portion properly placed and respectively showing loose and tightened purse string sutures to illustrating the gathering of tissue between the cannula anchor elements.
Figure 4B:
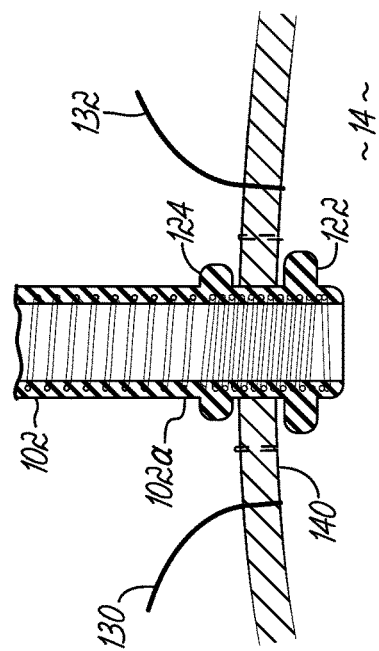

As further shown in FIGS. 4A and 4B, the purse string suture or sutures 130, 132 may be tightened to a degree that is adequate to provide a leak tight seal. In this regard, the tightened tissue 140 should at least substantially fill or gather within the gap between the distal and proximal anchor elements 122, 124 as schematically shown in FIG. 4B. If additional gathering of tissue 140 is necessary, additional tissue 140 may be gathered with one or more additional purse string sutures.

Figure 5:
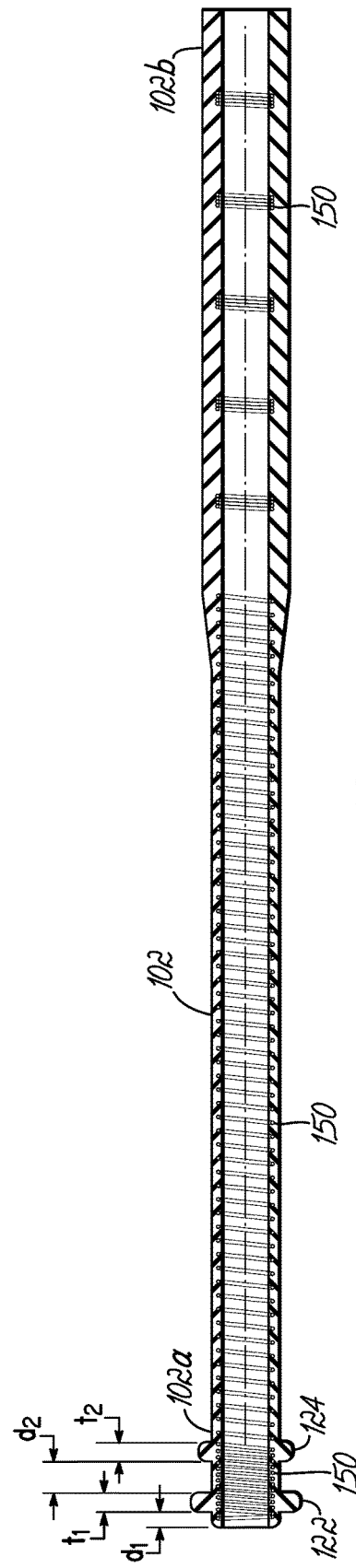
FIG. 5 is a longitudinal cross sectional view of the inflow cannula.

FIG. 5 illustrates the inflow cannula 102 in greater detail. In this embodiment, the cannula 102 may be approximately 10 mm in diameter, with the proximal anchor element 124 being 12 mm in diameter and the distal anchor element 122 being 14 mm in diameter. The tip dimension $d_1$ extending outwardly from the distal anchor element 122 is approximately 2 mm, while the thicknesses $t_1$, $t_2$ along the longitudinal axis of the cannula 102 of anchor elements 122, 124 are each approximately 2.5 mm. The distance $d_2$ between the distal and proximal anchor elements 122, 124 is approximately 4 mm. It will be appreciated that these dimensions are representative and illustrative in nature and may be changed according to the needs of any given case or patient. The inflow cannula 102, which may be constructed from surgical grade silicone, may also include reinforcements in the form of stainless steel or Nitinol coils 150. It is desirable to have the inflow cannula 102 as flexible as possible, but still of a design that prevents kinking. In view of the flexibility of the cannula 102, it may be necessary to provide stiffness to at least the distal end portion 102a during insertion through the wall of the heart at access location 110 (or any other desired location). This stiffness may be provided only temporarily during the insertion procedure. For example, a trocar (not shown) may be inserted temporarily through the proximal end 102b of cannula 102 and into the distal end portion 102a while inserting the cannula 102 into the heart 15 as described herein. To retain the distal end of the trocar in the distal end 102a of the cannula 102, there may be a balloon-like or other expandable element associated with the trocar that engages the interior of the distal end 102a during the cannula insertion process. After the cannula 102 is properly positioned as described herein, the trocar could be removed and the remainder of the implantation process, such as connection of the pump 104 and outflow cannula 106 could take place. A similar process may be used during a catheterization procedure as described herein.

Below, and as representative and nonlimiting examples, various surgical approaches are more fully described.

Surgical Open Sternotomy—This approach allows full access to the heart, especially the left atrium, and allows access to several different locations where a blood inflow cannula might be attached to the heart. However, due to the highly invasive nature of this approach, less invasive implantation approaches may be more desirable to a surgeon.

Surgical Open Thoracotomy—In this surgical approach, a relatively superior and caudal thoracotomy access is used to deliver the blood inflow cannula to the left atrium where it is anchored at a location on the roof of the atrium. This location on the atrium has specific benefit because the wall of the atrium is smooth and relatively large at this location, isolating the cannula tip from other structures within the atrium.

In another suitable surgical method, a relatively lateral thoracotomy access is used to deliver the blood inflow cannula to the left atrium where it is anchored at a location on the postero-medial wall near the interatrial septum. This location is often called "Waterson's groove" as discussed above and is a common location to make a left atriotomy when performing mitral valve repair surgery. Waterson's groove is accessed surgically by dissecting the left atrium away from the right atrium at this posterior aspect, between the superior vena cava and the left pulmonary veins.

Thoracoscopic Surgery—In this surgical method, the blood inflow cannula may be implanted in a similar location as described above in that a tubular trocar may be used to access the intra-thoracic location (Waterson's groove, for example) where the cannula would be anchored through the heart wall. In this minimally or less invasive surgical method, the entire operation is performed through these relatively small tubular trocars thereby minimizing the size of the opening in the patient's chest. Typically, additional small holes are made to deliver trocars used in conjunction with the main delivery trocar to allow placement of an endoscopic camera and specialized surgical tools for grasping, cutting, suturing, cauterizing, or performing other operations on tissue. Through the main trocar, the cannula can be delivered to the same location as in the open surgical technique (i.e. Waterson's groove) but with less invasive access across the chest wall.

Transluminal—This method of implantation can, for example, involve directing the blood inflow cannula from the heart to the superficial remote pump location via a transluminal route. This transluminal route may involve passing the cannula via the axillary and/or subclavian vein, through the superior vena cava into the left atrium and then anchoring the cannula into the left atrium by passing it through the intra-atrial septum, such as through the fossa ovalis. Alternatively, the cannula might enter/exit the venous vasculature at the jugular vein. The cannula proximal end may be routed to the superficial pectoral pump location by being tunneled under the skin or chest musculature.

Over-the-Wire (Seldinger) Technique—A method for implanting the cannula, whether in surgical or transluminal approaches, is to utilize a low profile and simple "over the wire" approach often called the Seldinger technique. The Seldinger technique for percutaneously placing a catheter into the lumen of a blood vessel involves inserting a needle into the vessel across its wall, and then following with a guide wire through the needle. Once the guide wire is placed across the skin into the vessel lumen, the needle can be removed and then a suitable catheter placed over the wire into the vessel lumen. This technique minimizes trauma to the vessel wall, as often the hole across the vessel wall is gently expanded or dilated by the catheter being introduced. Another key advantage of the technique is that blood loss is minimized because control of the hole size around whatever is inserted is maintained. As an example, the transluminal cannula could be introduced into the jugular or subclavian vein after access to the vessel is obtained using the percutaneous Seldinger technique, where the cannula would be adapted to be introduced into the vessel over the guide wire. Such adaptations would include an obturator or dilator within the inner lumen of the cannula and thereby providing support and lumen size matching to facilitate dilation and blood maintenance through the puncture site. Once the cannula is introduced via the percutaneous puncture site, a surgical tunnel from the pectoral pocket location of the pump may be made up to the subcutaneous location of the veinotomy, where the exposed end of the cannula would be secured and pulled through the tunnel to the pump pocket.

Alternatively, a variation of the Seldinger technique might be utilized in the various surgical implantation approaches described above, where the cannula system would be specifically adapted to facilitate this implantation technique. Although the Seldinger technique is most commonly associated with percutaneous access to blood vessels, an adapted version of the technique utilizing a specifically adapted cannula introduction system is a highly preferred approach to surgical implantation where direct access to the heart itself is utilized. Here, for example, an atriotomy could be made by inserting a needle across the heart wall and a guide wire then placed therethrough. After removal of the needle, with bleeding controlled and minimal, the cannula system with specialized introduction obturator within can be introduced over the wire thereby maintaining many of the advantages of the so-called Seldinger technique even in a surgical approach.

While the present invention has been illustrated by a description of various illustrative embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or any combinations depending on the needs and preferences of the user. However, the invention itself should only be defined by the appended claims.

What is claimed is:

1. A device for establishing a blood flow conduit between a chamber in a heart of a patient and a remote location, the device comprising:
   a cannula having an outer surface, proximal and distal end portions, and a lumen extending between the proximal and distal end portions, the distal end portion including an opening communicating with the lumen of the cannula for allowing blood flow therethrough, the distal end portion and opening being configured for insertion into the chamber of the heart; and
   first and second anchor elements permanently fixed to the outer surface of the cannula and having respective maximum width dimensions extending radially outwardly from the outer surface of the cannula, the first anchor element being positioned more distally than the second anchor element and defining a tissue-receiving space therebetween, and the maximum width dimension of the first anchor element being larger than the maximum width dimension of the second anchor element, whereby the first anchor element is configured to be positioned inside the heart chamber and the second anchor element is configured to be positioned outside the heart chamber with heart tissue held in the tissue-receiving space therebetween and the first and second anchor elements are each further configured to directly contact the heart tissue therebetween.

2. The device of claim 1, wherein at least one of the first or second anchor elements further comprises an annular disc shaped element.

3. The device of claim 1, wherein at least one of the first or second anchor elements is formed from a pliable, resilient material.

4. The device of claim 1, wherein the cannula is a blood flow catheter configured to be introduced into the venous system of the patient in order to percutaneously direct the distal end portion into the chamber of the heart.

5. The device of claim 4, wherein the first and second anchor elements are configured to be movable between first, compact states during introduction via the venous system and second, expanded states for positioning on opposite sides of the heart tissue.

6. The device of claim 5, wherein the first and second anchor elements are self-expandable into the second, expanded states.

7. The device of claim 1, wherein the first and second anchor elements are formed to allow ingrowth of tissue.

8. A catheter system for establishing a blood flow conduit between a chamber in a heart of a patient and a remote location, the system comprising:
   a delivery catheter;
   a blood inflow catheter configured to be directed into the venous system of the patient via the delivery catheter, the blood inflow catheter having an outer surface, proximal and distal end portions, and a lumen extending between the proximal and distal end portions, the distal end portion is configured to be inserted into the chamber of the heart and includes an opening that communicates with the lumen for allowing blood flow therethrough; and first and second anchor elements carried on and permanently fixed to the distal end portion and having respective maximum width dimensions extending radially outwardly from the outer surface of the blood inflow catheter, the first anchor element being positioned more distally than the second anchor element and defining a tissue-receiving space therebetween, and the maximum width dimension of the first anchor element being larger than the maximum width dimension of the second anchor element, whereby the first anchor element is configured to be positioned inside the heart chamber and the second anchor element is configured to be positioned outside the heart chamber such that heart tissue is held in the tissue-receiving space therebetween and the first and second anchor elements are each further configured to directly contact the heart tissue therebetween.

9. The system of claim 8, wherein at least one of the first or second anchor elements further comprises an annular disc shaped element.

10. The system of claim 8, wherein at least one of the first or second anchor elements is formed from a pliable, resilient material.

11. The system of claim 8, wherein the first and second anchor elements are configured to be movable between first, compact states during introduction via the venous system and second, expanded states for positioning on opposite sides of the heart tissue.

12. The system of claim 11, wherein the first and second anchor elements are self-expandable into the second, expanded states.

13. The system of claim 12, wherein the delivery catheter is configured to be a restraining member to maintain the first and second anchor elements in the first, compact states.

14. The system of claim 8, wherein the first and second anchor elements are formed to allow ingrowth of tissue.

15. A supplemental blood flow assist device for increasing blood flow between a chamber in a heart of a patient and a remote location in the circulatory system of the patient, the device comprising:
 a blood pump having an inlet and an outlet, the outlet being adapted for connection to the remote location in the circulatory system of the patient;
 a cannula having an outer surface, proximal and distal end portions, and a lumen extending between the proximal and distal end portions, the proximal end portion being configured to be coupled to the inlet of the blood pump and the distal end portion is configured to be inserted into the chamber of the heart and having an opening that communicates with the lumen of the cannula for allowing blood flow therethrough; and
 first and second anchor elements carried on and permanently fixed to the distal end portion and having respective maximum width dimensions extending radially outwardly from the outer surface of the cannula, the first anchor element being positioned more distally than the second anchor element and defining a tissue-receiving space therebetween, and the maximum width dimension of the first anchor element being larger than the maximum width dimension of the second anchor element, whereby the first anchor element is configured to be positioned inside the heart chamber and the second anchor element is configured to be positioned outside the heart chamber with heart tissue held in the tissue-receiving space therebetween and the first and second anchor elements are each further configured to directly contact the heart tissue therebetween.

16. The device of claim 15, wherein at least one of the first or second anchor elements further comprises an annular disc shaped element.

17. The device of claim 15, wherein at least one of the first or second anchor elements is formed from a pliable, resilient material.

18. The device of claim 15, wherein the cannula is a blood flow catheter configured to be introduced into the venous system of the patient in order to percutaneously direct the distal end portion into the chamber of the heart.

19. The device of claim 18, further comprising a delivery catheter configured to receive the blood flow catheter such that the distal end portion of the blood flow catheter is deliverable to the heart.

20. The device of claim 18, wherein the first and second anchor elements are configured to be movable between first, compact states during introduction via the venous system and second, expanded states for positioning on opposite sides of the heart tissue.

21. The device of claim 20, wherein the first and second anchor elements are self-expandable into the second, expanded states.

22. The device of claim 15, wherein the first and second anchor elements are formed to allow ingrowth of tissue.

23. A method of establishing blood flow from a chamber in a heart of a patient to a remote location for providing supplemental blood flow from the heart, the method comprising:
 inserting at least a portion of a distal end portion of a cannula into the chamber of the heart, the distal end portion including an opening that is in fluid communication with a lumen of the cannula for allowing blood flow therethrough, the distal end portion further including first and second anchor elements permanently fixed thereto, each anchor element having a maximum width dimension in a direction perpendicular to a lengthwise axis of the cannula, the lengthwise axis extending from a proximal end portion of the cannula to the distal end portion, and the first anchor element having a larger maximum width dimension than the second anchor element;
 placing the first anchor element inside the chamber and contacting an inside surface of tissue defining the chamber; and
 placing the second anchor element outside the chamber and contacting an outside surface of the tissue defining the chamber.

24. The method of claim 23, wherein placing the first and second anchor elements further comprises:
 pushing the first and second anchor elements into the chamber; and
 pulling only the second anchor element outside of the chamber thereby leaving the first anchor element inside the chamber.

25. The method of claim 23, wherein the cannula is a catheter, and inserting at least a portion of a distal end portion of the catheter further comprises directing the catheter through the venous system of the patient from a location remote from the heart.

26. The method of claim 23, further comprising:
 connecting the proximal end portion of the cannula in fluid communication with a blood pump located remotely from the heart of the patient.

27. The method of claim 23, further comprising:
 tightening the tissue between the first and second anchor elements.

28. The method of claim 27, wherein tightening the tissue further comprises:
applying at least one purse string suture to the tissue.

29. A method of establishing blood flow from a chamber in a heart of a patient to a remote location for providing supplemental blood flow from the heart, the method comprising:
inserting a distal end portion of a cannula into the chamber of the heart, the distal end portion including an opening in fluid communication with a lumen of the cannula for allowing blood flow therethrough, the distal end portion further including first and second anchor elements permanently fixed thereto, with the first anchor element being located more distally than the second anchor element and a tissue-receiving space being located between the first and second anchor elements, the first and second anchor elements each having respective maximum width dimensions extending radially outwardly from an outer surface of the cannula, the maximum width dimension of the first anchor element being larger than the maximum width dimension of the second anchor element;
pulling the more proximally-located second anchor element out of the chamber;
engaging the more proximally-located second anchor element in contact with an outside surface of tissue defining the chamber; and
engaging the first anchor element in contact with an inside surface of the chamber such that the tissue is retained in the tissue-receiving space and the cannula is in fluid communication with the chamber.

30. The method of claim 29, wherein the cannula is a catheter, and inserting the distal end further comprises:
directing the distal end portion through the venous system of the patient from a location remote from the heart.

31. The method of claim 29, wherein at least the second anchor element is resilient and pliable, and the pulling the second anchor element out of the chamber further comprises forcing the second anchor element through an aperture in the tissue such that the anchor element assumes a more compact state until the second anchor element emerges from the aperture at a location outside the chamber.

32. The method of claim 29, wherein the chamber is the left atrium of the heart.

33. The method of claim 29, further comprising:
connecting the proximal end portion of the cannula in fluid communication with a blood pump located remotely from the heart of the patient.

34. The method of claim 29, further comprising:
tightening the tissue between the first and second anchor elements.

35. The method of claim 34, wherein tightening the tissue further comprises:
applying at least one purse string suture to the tissue.

36. A cannula system for establishing blood flow between a chamber of a heart and a remote location, comprising:
a trocar;
a cannula including proximal and distal end portions and a lumen extending therebetween that is configured to receive the trocar therein, the cannula further including first and second anchor elements permanently fixed to the distal end portion and having respective maximum width dimensions extending radially outwardly from the outer surface of the cannula, the first anchor element being positioned more distally than the second anchor element and defining a tissue-receiving space therebetween and the first and second anchor elements are each further configured to directly contact the heart tissue therebetween, and the maximum width dimension of the first anchor element being larger than the maximum width dimension of the second anchor element; and
an expandable element associated with the trocar and configured to temporarily engage the interior of the cannula during a process of inserting the distal end into the heart chamber.

37. The cannula system of claim 36, wherein the expandable element further comprises a balloon-like element.

* * * * *